(12) United States Patent
Blanda et al.

(10) Patent No.: US 9,919,028 B2
(45) Date of Patent: Mar. 20, 2018

(54) AUTOCLAVABLE SUSPENSIONS OF CYCLOSPORIN A FORM 2

(71) Applicant: Allergan, Inc., Irvine, CA (US)

(72) Inventors: Wendy M. Blanda, Tustin, CA (US); Hongwen Ma Rivers, San Marcos, CA (US); David A. Marsh, Irvine, CA (US); Michelle Luu, Anaheim, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 15/171,866

(22) Filed: Jun. 2, 2016

(65) Prior Publication Data

US 2016/0271207 A1 Sep. 22, 2016

Related U.S. Application Data

(62) Division of application No. 13/676,362, filed on Nov. 14, 2012, now abandoned.

(60) Provisional application No. 61/559,849, filed on Nov. 15, 2011.

(51) Int. Cl.
| | |
|---|---|
| *A61K 38/13* | (2006.01) |
| *A61K 47/38* | (2006.01) |
| *A61K 47/32* | (2006.01) |
| *A61K 9/00* | (2006.01) |
| *A61K 47/36* | (2006.01) |
| *C07K 1/30* | (2006.01) |
| *C07K 7/64* | (2006.01) |

(52) U.S. Cl.
CPC .......... *A61K 38/13* (2013.01); *A61K 9/0048* (2013.01); *A61K 47/32* (2013.01); *A61K 47/36* (2013.01); *A61K 47/38* (2013.01); *C07K 1/306* (2013.01); *C07K 7/645* (2013.01)

(58) Field of Classification Search
CPC ........ A61K 38/13; A61K 47/32; A61K 47/38; A61K 47/36; A61K 9/0048; C07K 1/306; C07K 7/645
See application file for complete search history.

(56) References Cited

U.S. PATENT DOCUMENTS

| | | |
|---|---|---|
| 5,474,979 A | 12/1995 | Ding et al. |
| 5,981,607 A | 11/1999 | Ding et al. |
| 6,254,860 B1 | 7/2001 | Garst |
| 6,350,442 B2 | 2/2002 | Garst |
| 6,551,619 B1 | 4/2003 | Penkler et al. |
| 7,153,834 B2 | 12/2006 | Patel |
| 2001/0041671 A1 | 11/2001 | Napoli |
| 2005/0059583 A1 | 3/2005 | Acheampong et al. |
| 2006/0100288 A1 | 5/2006 | Bague et al. |
| 2006/0148686 A1 | 7/2006 | Xia et al. |
| 2007/0015691 A1 | 1/2007 | Chang et al. |
| 2008/0009436 A1 | 1/2008 | Chang |
| 2009/0312429 A1 | 12/2009 | Safonova et al. |
| 2013/0023482 A1 | 1/2013 | Gore et al. |

FOREIGN PATENT DOCUMENTS

| | | |
|---|---|---|
| GB | 2211848 A | 7/1989 |
| WO | 1995031211 A1 | 11/1995 |
| WO | 2002087563 A1 | 11/2002 |
| WO | 2005-072701 | 8/2005 |
| WO | 2009-088570 | 7/2009 |
| WO | WO2010141586 A3 | 3/2011 |
| WO | WO2011049958 A3 | 9/2011 |
| WO | 2012-166610 A1 | 12/2012 |

OTHER PUBLICATIONS

Cedarstaff, Thomas et al, A Comparative Study of Tear Evaporation Rates and Water Content of Soft Contact Lenses, American Journal of Optometry & Physiological Optics, 1983, 167-174, 60(3).
Definition of cyclosporine, from http://medical-dictionary.thefreedictionary.com/p/cyclosporine, pp. 1-5, accessed Mar. 27, 2014.
Hyaluronic Acid, from http://www.hyalogic.com/main/about_hyaluronic_acid, pp. 1-6, accessed Apr. 11, 2014.
Lechuga-Ballesteros, David et al, Properties and Stability of a Liquid Crystal Form of Cyclosporine—The First Reported Naturally occurring Peptide That Exists as a Thermotropic Liquid Crystal, Journal of Pharmaceutical Sciences, Sep. 2003, 1821-1831, 92(9).
Maleki, Atoosa, et al., Anomaloous Vicosity Behavior in Aqueous Solutions of Hyaluronic Acid, Polymer Bulletin, Sep. 2007, 217-226, vol. 59, Issue 2, Springer.
Parenteral Routes of Administration, from Study online at quizlet.com/_6z8rb, pp. 1-2, accessed Oct. 1, 2014.
Syringe Needle Gauge Chart, from http://sigmaaldrich.com/chemistry/stockroom-reagents/learning-center/technical-library, pp. 1-2, accessed Oct. 1, 2014.
Wilson, et al., How to Give Intravitreal Injections, Eyenet Magazine, 2013, 45-47.

*Primary Examiner* — Julie Ha
*Assistant Examiner* — Li Ni Komatsu
(74) *Attorney, Agent, or Firm* — Laura L. Wine

(57) ABSTRACT

Disclosed herein are autoclavable formulations of cyclosporin A Form 2, methods of making such formulations, and methods of treating diseases of the eye with such formulations.

2 Claims, 12 Drawing Sheets

AUTOCLAVABLE SUSPENSIONS OF CYCLOSPORIN A FORM 2

CROSS-REFERENCE TO RELATED APPLICATION

This patent application is a divisional of copending U.S. patent application Ser. No. 13/676,362, filed Nov. 14, 2012, now abandoned, which claims priority to U.S. Provisional Patent Application No. 61/559,849, filed Nov. 15, 2011, the entire contents of which are hereby incorporated by reference.

BACKGROUND

Aseptic processing of cyclosporin A suspensions in a hyaluronic acid media (a hydrogel used as a suspending agent), is complicated by the fact that both the drug and the hyaluronic acid need to be pre-sterilized. Pre-sterilized hyaluronic acid is extremely expensive, costing roughly $1 million dollars for a few kilograms (roughly $10,000 per ounce) of sterile raw material. Additionally, in the process of pre-sterilizing cyclosporin A, the drug is degraded upon irradiation, as shown below and in FIGS. 1 and 2:

TABLE 1

Impact of Irradiation on Cyclosporin Stability

| Sterilization Mode | Form 1 CsA (Potency and Imp.) | Form 2 CsA (Potency and Imp.) | Form 3 CsA (Potency and Imp.) | Amorph, CsA (Potency and Imp.) |
| --- | --- | --- | --- | --- |
| None | 98.4% w/w<br>Total Imp: 0.6% | 94.6% w/w<br>Total Imp: 0.6% | 97.7% w/w<br>Total Imp: 0.8% | 96.5% w/w<br>Total Imp: 0.7% |
| 15 kGy Gamma | 93.9% w/w<br>% Rel. Change: 4.5%<br>Total Imp: 1.7% | 91.8% w/w<br>% Rel. Change: 2.9%<br>Total Imp: 1.8% | 94.3% w/w<br>% Rel. Change: 3.6%<br>Total Imp: 1.3% | 92.1% w/w<br>% Rel. Change: 4.6%<br>Total Imp: 1.4% |
| 30 kGy Gamma | 90.7% w/w<br>% Rel. Change: 7.8%<br>Total Imp: 2.8% | 88.5% w/w<br>% Rel. Change: 6.4%<br>Total Imp: 2.4% | 91.0% w/w<br>% Rel. Change: 6.9%<br>Total Imp: 2.3% | 87.7% w/w<br>% Rel. Change: 9.2%<br>Total Imp: 2.3% |
| E-Beam | 92.6% w/w<br>% Rel. Change: 5.9%<br>Total Imp: 1.5% | 90.3% w/w<br>% Rel. Change: 4.6%<br>Total Imp: 1.7% | 93.4% w/w<br>% Rel. Change: 4.5%<br>Total Imp: 1.6% | 92.0% w/w<br>% Rel. Change: 4.7%<br>Total Imp: 1.3% |

Cooling the cyclosporin during irradiation does not significantly improve the results, as shown in Table 2, below:

TABLE 2

Impact on Cyclosporin Stability after irradiation under Cold Conditions

| Sterilization Mode | Form 1 CsA (Potency and Imp.) | Form 2 CsA (Potency and Imp.) | Form 3 CsA (Potency and Imp.) | Amorph, CsA (Potency and Imp.) |
| --- | --- | --- | --- | --- |
| None | 99.4% w/w<br>Total Imp: 0.7% | 97.6% w/w<br>Total Imp: 0.5% | 98.4% w/w<br>Total Imp: 0.7% | 96.5% w/w<br>Total Imp: 0.7% |
| Cold E-beam | 94.6% w/w<br>% Rel. Change: 4.8%<br>Total Imp: 1.5% | 91.1% w/w<br>% Rel. Change: 6.7%<br>Total Imp: 1.5% | 94.6% w/w<br>% Rel. Change: 3.9%<br>Total Imp: 1.8% | 92.3% w/w<br>% Rel. Change: 4.4%<br>Total Imp: 1.3% |
| Regular E-Beam (from Previous Study) % Relative Change in Potency on Sterilization | % Rel. Change: 5.9%<br>Total Imp: 1.5% | % Rel. Change: 4.6%<br>Total Imp: 1.7% | % Rel. Change: 4.5%<br>Total Imp: 1.6% | % Rel. Change: 4.7%<br>Total Imp: 1.3% |

Additional levels of degradants need to be qualified in preclinical safety studies. Moreover, a suspension, prepared with only 90-95% of the labeled Cyclosporin A (due to the pre-sterilization process), has a substantial probability of failure to meet regulatory guidelines for shelf-life, since regulatory authorities generally prohibit shelf-lives below 90% of label.

The present invention solves these problems. Disclosed herein are formulations of cyclosporin A, combined with a parenterally-biocompatible suspending agent, which are sterile, exceptionally stable to heat sterilization, and have excellent long-term stability.

DETAILED DESCRIPTION

Cyclosporin A

Cyclosporin A (CsA) is a cyclic peptide having the following chemical structure:

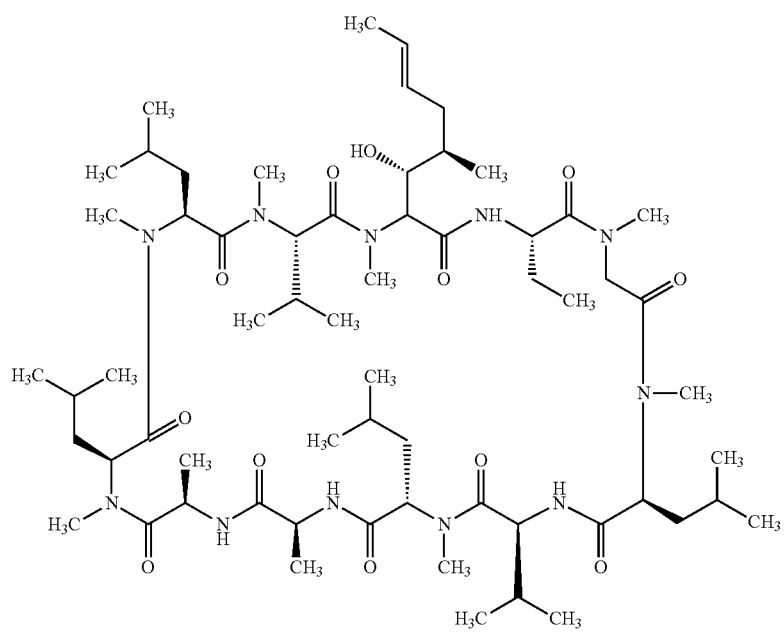 [SMILES: C/C=C/C[C@@H](C)[C@@H](O)C1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

Its chemical name is cyclo[(E)-(2S,3R,4R)-3-hydroxy-4-methyl-2-(methylamino)-6-octenoyl]-2-aminobutyryl-N-methylglycyl-N-methyl-L-leucyl-L-valyl-N-methyl-L-leucyl-L-alanyl-D-alanyl-N-methyl-L-leucyl-N-methyl-L-leucyl-N-methyl-L-valyl]. It is also known by the names cyclosporin, cyclosporine A, ciclosporin, and ciclosporin A. It is the active ingredient in Restasis® (Allergan, Inc., Irvine, Calif.), an emulsion comprising 0.05% (w/v) cyclosporin. Restasis® is approved in the United States to increase tear production in patients whose tear production is presumed to be suppressed due to ocular inflammation associated with keratoconjunctivitis sicca.

Cyclosporin A Form 2

Cyclosporin A is known to exist in an amorphous form, liquid crystal form, tetragonal crystalline form (form 1), and an orthorhombic form (form 3). A new crystalline form, cyclosporin A Form 2, has recently been discovered.

Figure 1:
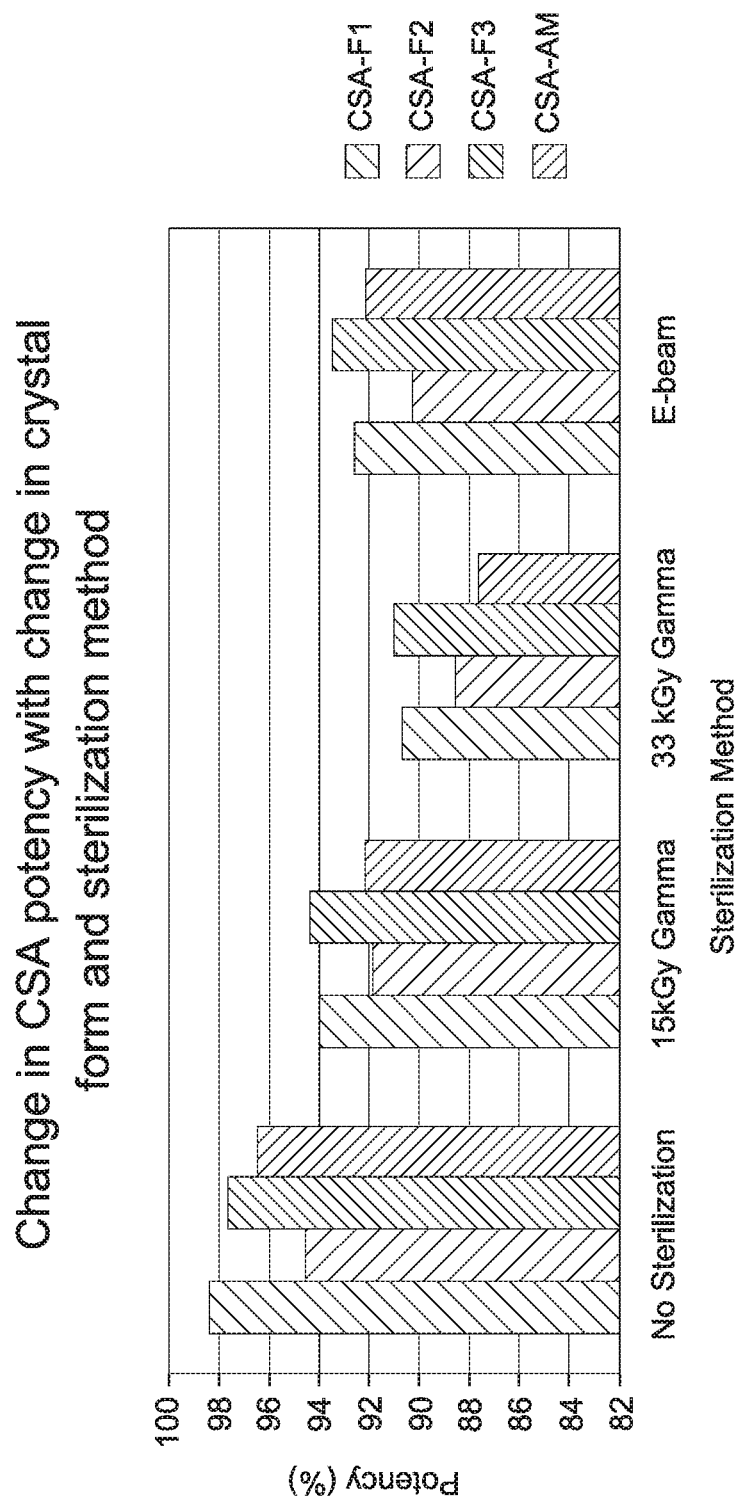
FIGS. 1 and 2 show change in cyclosporin A potency with change in crystal form and sterilization method.

The XRPD pattern of CsA Form 2 differs significantly from the tetragonal form and orthorhombic form (FIG. 1). The major crystalline peaks for CsA form 2 appear at (2θ) when scanned by an X-ray diffractometer with X-ray source as Cu Kα radiation, A=1.54 Å, at 30 kV/15 mA: 7.5, 8.8, 10.2, 11.3, 12.7, 13.8, 14.5, 15.6 and 17.5 (d-spacing in crystal lattice at about 11.8, 10.0, 8.7, 7.8, 7.0, 6.4, 6.1, 5.6 and 5.1 Å, respectively, FIG. 2). These major peaks are defined as those being unique to Form 2 relative to the orthorhombic or tetragonal forms; as well as, peaks having an intensity greater than 5 times the background.

In one embodiment, the new crystalline form (Form 2) of CsA is a nonstoichiometric hydrate of Cyclosporin A. In another embodiment, the crystalline Form 2 is represented by the formula:

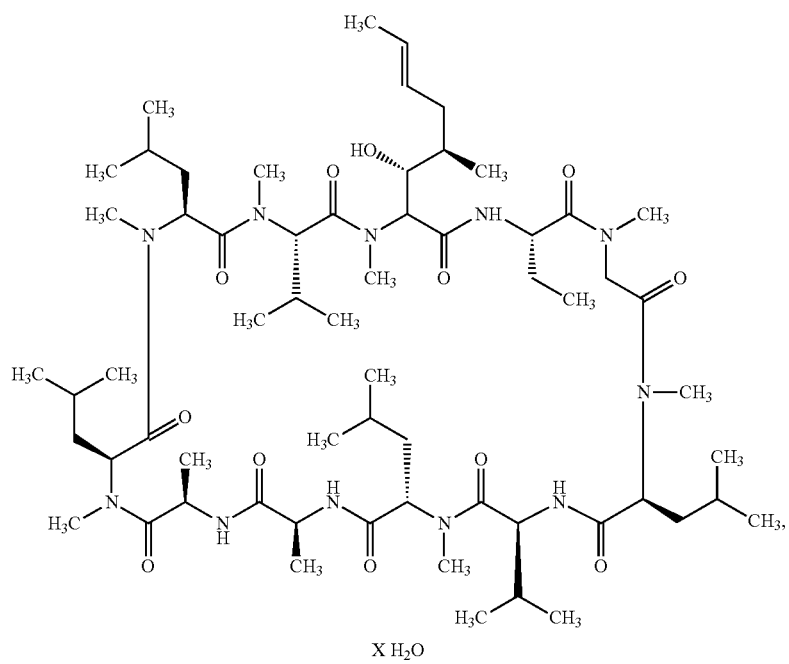

X H₂O wherein X is the number of molecules of water and varies from 0 to 3. In one embodiment, X in the above formula is 2.

Form 2 appears to be a kinetically stable form of CsA in aqueous suspensions. Suspensions containing Form 2 show no conversion to other known polymorphic or pseudomorphic forms upon storage. It has been found that Form 1 and the amorphous form convert to Form 2 in the presence of water.

The single crystal structure of the hydrate form of CsA Form 2 has been determined and the crystal structure parameters are listed in Table 2. These results indicate that Form 2 is unique compared to other known crystalline forms of cyclosporin A.

TABLE 1

Crystal data and data collection parameters of crystal structure solution of CsA Form 2.

| | |
|---|---|
| formula | $C_{62}H_{115}N_{35}O_{14}$ |
| formula weight | 1236.67 |
| space group | P $2_1$ $2_1$ $2_1$ (No. 19) |
| a (Å) | 12.6390 (5) |
| b (Å) | 19.7582 (8) |
| c (Å) | 29.588 (2) |
| volume (Å³) | 7383.8 (7) |
| Z | 4 |
| $d_{calc}$ (g cm⁻³) | 1.114 |
| crystal dimensions (mm) | 0.27 × 0.18 × 0.12 |
| temperature (K) | 150 |
| radiation (wavelength in Å) | Cu K₂ (1.54184) |
| monochromator | confocal optics |
| linear abs coef (mm⁻¹) | 0.840 |
| absorption correction applied | empirical[a] |
| transmission factors (min, max) | 0.80, 0.93 |
| diffractometer | Rigaku RAPID-II |
| h, k, l range | −13 to 13 −21 to 21 −32 to 21 |
| 2θ range (deg) | 5.38-115.00 |
| mosaicity (deg) | 1.31 |
| programs used | SHELXTL |
| $F_{exo}$ | 2704.0 |

TABLE 1-continued

Crystal data and data collection parameters of crystal structure solution of CsA Form 2.

| | |
|---|---|
| weighting | $1/[\sigma^2(Fo^2) + (0.0845P)^2 + 0.0000P]$ where P = $(Fo^2 + 2Fc^2)/3$ |
| data collected | 37360 |
| unique data | 9964 |
| $R_{exo}$ | 0.077 |
| data used in refinement | 9964 |
| cutoff used in R-factor calculations | $Fe^2 > 2.0s(Fe_a^2)$ |
| data with I > 2.0s(I) | 6597 |
| number of variables | 834 |
| targest shift/esd in final cycle | 0.00 |
| $R(F_a)$ | 0.061 |
| $R_*(F_a^2)$ | 0.145 |
| goodness of fit | 1.037 |
| absolute structure determination | Flack parameter[a] (0.0(3)) |

Figure 12:
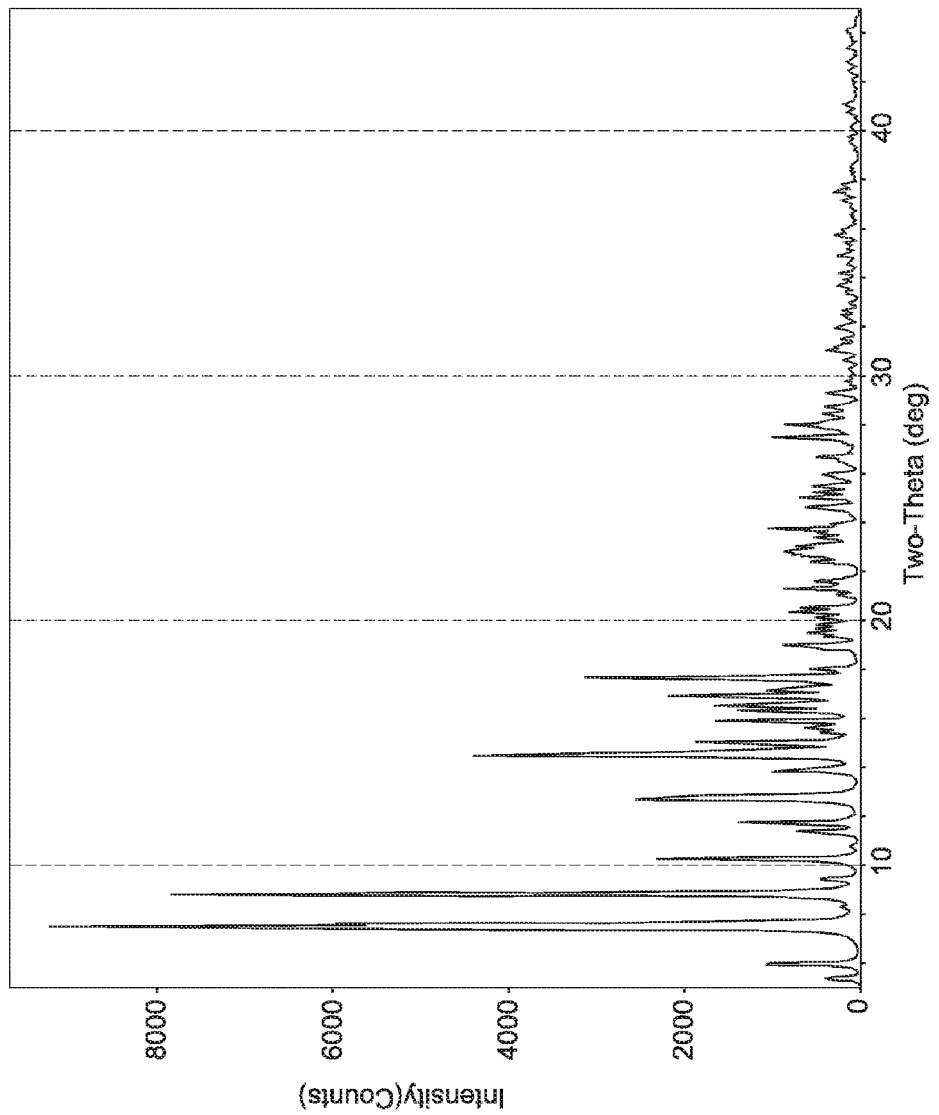
FIG. 12 shows the simulated XRPD pattern of cyclosporin A forms.

The asymmetric unit of this CsA Form 2 contains one cyclosporin A molecule and two water molecules. It is possible that any small molecule that can hydrogen bond to water could play the role of space filler, which would give a range of potential structures running from the orthorhombic dihydrate to distorted monoclinic dihydrate The XRPD pattern calculated from the single-crystal structure is shown in FIG. 12 and it matches the experimental pattern shown in FIG. 2. These matching patterns further corroborate that Form 2 is a unique and pure crystalline form of cyclosporin A.

Figure 7:
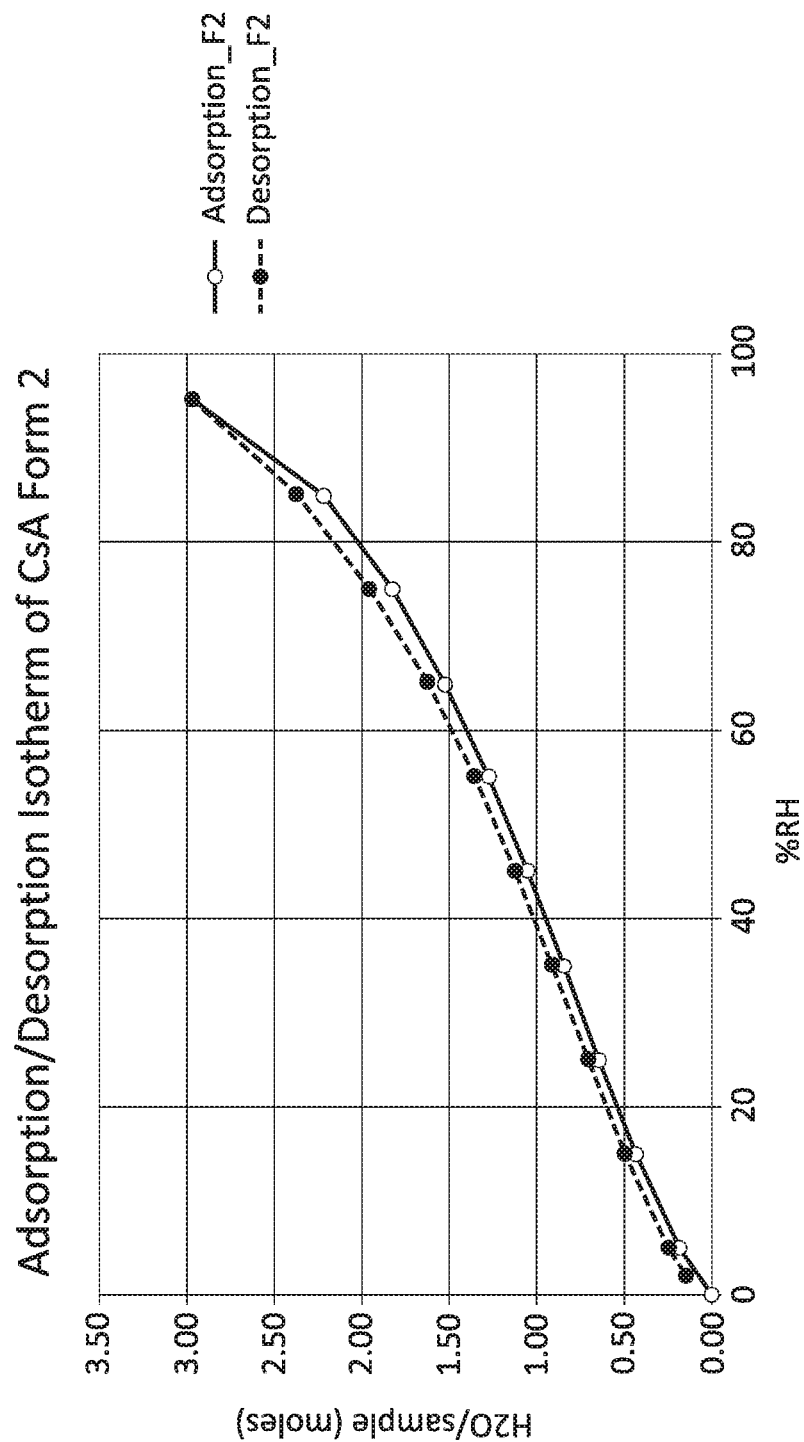
FIG. 7 depicts the water sorption/desorption profile of CsA Form 2.
Figure 8:
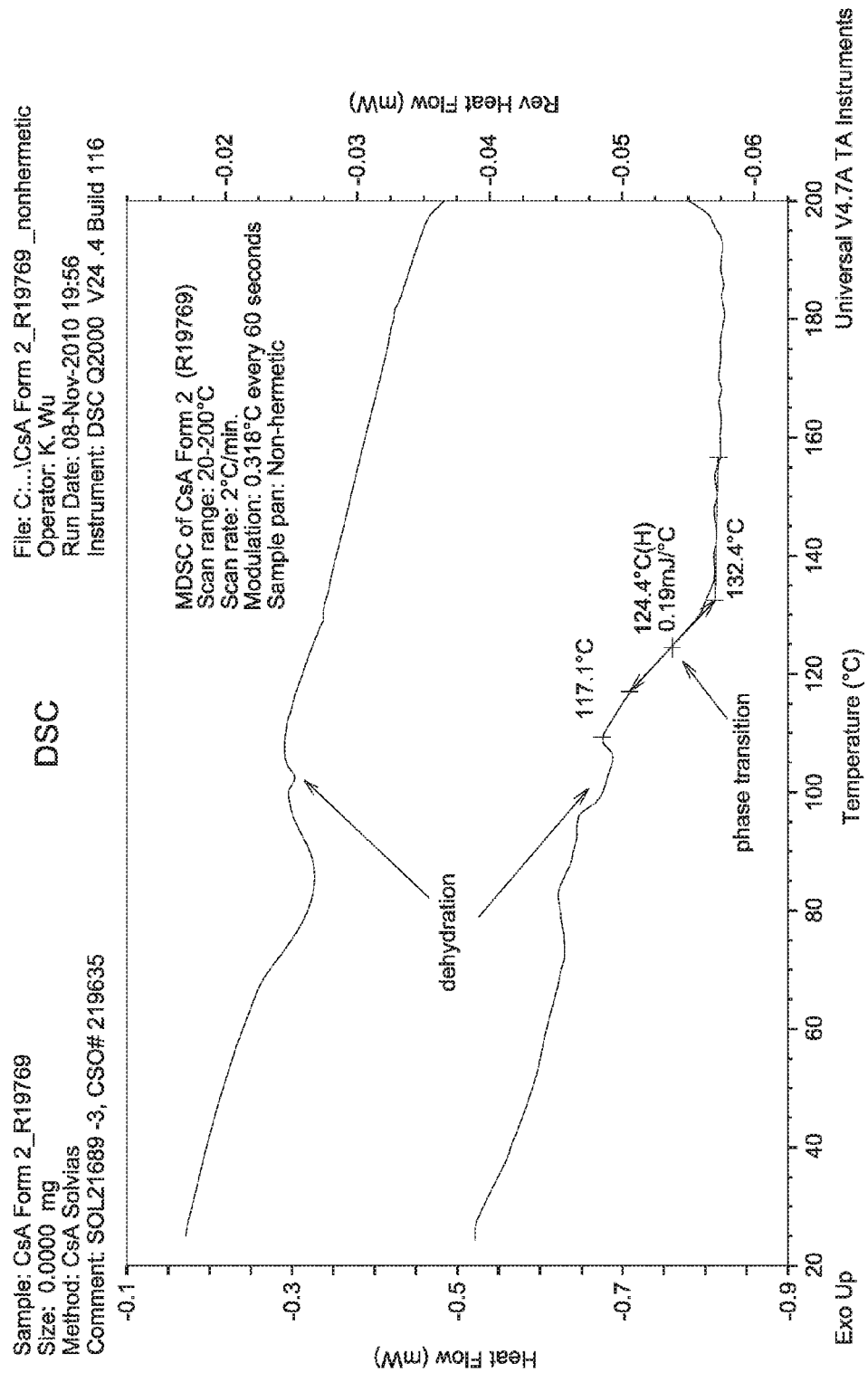
FIG. 8 depicts MDSC analysis of CsA Form 2 recovered from 0.04% formulation with 1% PS80.

Without wishing to be bound by theory, thermogravimetric analysis combined with KF titration and vapor sorption desorption analysis (VSA) suggest that CsA Form 2 is a non-stoichiometric hydrate of CsA. The vapor sorption analysis of Cyclosporin Form 2 indicates that water content in the new crystal form reversibly varies with relative humidity as shown in FIG. 7. Similar to the tetragonal form, the new CsA form undergoes a phase transition to a liquid crystal or amorphous form at 124.4° C. prior to melting as indicated by the modulated differential calorimetric (MDSC) analysis (FIG. 8).

Cyclosporin A Form 2 may be obtained by suspending amorphous 0.05% cyclosporin A (w/v) in 1% Polysorbate 80, heating the solution to 65° C., holding it at that temperature for 24 hours, and then recovering the precipitate by vacuum filtration. One can then use the cyclosporin A Form 2 thus obtained to generate additional amounts, using Cyclosporin A Form 2 as a seed crystal; in this method, one suspends about 30 g cyclosporin A in a solution of 900 ml water containing 1% (w/v) Polysorbate 80, heats the solution to 65° C., and then seeds it with 0.2 g of cyclosporin A Form 2 at a temperature of 52° C. The solution is then stirred for about 22 hours at a temperature of between about 61° C. and 65° C., and then recovers the precipitate that results.

Further details regarding CsA Form 2 may be found in U.S. patent application Ser. No. 13/480,710, the entire contents of which are incorporated by reference herein.

Heat-Stable, Heat-Sterilized Suspensions of Cyclosporin A Form 2

Compositions of the invention are ophthalmically acceptable suspensions of Cyclosporin A form 2. By "ophthalmically acceptable," the inventors mean that the suspensions are formulated in such a way as to be non-irritating when administered to the eye of a mammal, such as a human.

The suspensions of the invention comprise cyclosporin A form 2 and a vehicle comprising a suspending agent such as hyaluronic acid, a cellulose, polyvinylpyrrolidone (PVP), Pluronic® copolymers based on ethylene oxide and propylene oxide, and Carbopol® polymers.

In one embodiment, the suspension comprises cyclosporin A Form 2 at a concentration of about 0.001% to about 10% (w/v). In one embodiment, the suspension comprises cyclosporin A form 2 at a concentration of about 0.001% (w/v) to about 0.01%, about 0.001% (w/v) to about 0.04% (w/v), about 0.001% (w/v) to about 0.03% (w/v), about 0.001% (w/v) to about 0.02% (w/v), or about 0.001% (w/v) to about 0.01% (w/v). In another embodiment, the suspension comprises cyclosporin A form 2 at a concentration of about 0.01% (w/v) to about 0.05%, about 0.01% (w/v) to about 0.04%, about 0.01% (w/v) to about 0.03% (w/v), about 0.01% (w/v) to about 0.02% (w/v), or about 0.01% (w/v) to about 0.01% (w/v). In another embodiment, the suspension comprises cyclosporin A form 2 at a concentration of about 0.01% (w/v) to about 0.1%, about 0.1% (w/v) to about 0.5%, about 0.01% (w/v) to about 1% (w/v), or about 1% (w/v) to about 10%.

For example, the suspensions may comprise about 0.001% (w/v), about 0.002% (w/v), about 0.003% (w/v), about 0.004% (w/v), about 0.005% (w/v), about 0.006% (w/v), about 0.007% (w/v), about 0.008% (w/v), about 0.009% (w/v), about 0.01% (w/v), about 0.015% (w/v), about 0.02% (w/v), about 0.025% (w/v), about 0.03% (w/v), about 0.035% (w/v), about 0.04% (w/v), about 0.045% (w/v), about 0.05% (w/v), about 0.055% (w/v), about 0.06% (w/v), about 0.065% (w/v), about 0.07% (w/v), about 0.075% (w/v), about 0.08% (w/v), about 0.085% (w/v), about 0.09% (w/v), about 0.095% (w/v), about 0.1% (w/v), about 0.15% (w/v), about 0.2% (w/v), about 0.25% (w/v), about 0.3% (w/v), about 0.35% (w/v), about 0.4% (w/v), about 0.45% (w/v), about 0.5% (w/v), about 0.55% (w/v), about 0.6% (w/v), about 0.65% (w/v), about 0.7% (w/v), about 0.75% (w/v), about 0.8% (w/v), about 0.85% (w/v), about 0.9% (w/v), about 0.95% (w/v), or about 1.0% (w/v) cyclosporin A form 2.

Examples are provided in Table 3, below:

TABLE 3

Autoclavable suspensions of cyclosporin A Form 2.

| Formulation | CsA (Crystal form) | CsA (%) | Gelling Agent (Type) | Gelling Agent (%) | Autoclave Conditions (Temp (° C.)/min) |
|---|---|---|---|---|---|
| 1 | 2 | 20 | CMC | 5 | 121/10 |
| 2 | 3 | 20 | CMC | 3 | 121/10 |
| 3 | NA | 0 | Carbopol Ultrez 10 | 1.5 | 121/15 |
| 4 | NA | 0 | Carbopol Ultrez 10 | 2.0 | 121/15 |
| 5 | NA | 0 | Carbopol Ultrez 10 | 2.5 | 121/15 |
| 6 | NA | 0 | Carbopol Ultrez 10 | 1.0 | 121/15 |
| 7 | NA | 0 | Carbopol Ultrez 10 | 4.0 | 121/15 |
| 8 | 2 | 5 | CMC | 3 | 121/15 |
| 9 | 2 | 5 | CMC | 2 | 121/15 |
| 10 | 2 | 20 | CMC | 10 | 121/15 |
| 11 | 2 | 0 | CMC | 10 | 121/15 |
| 12 | 2 | 5 | HPMC | 3 | 121/15 |
| 13 | 2 | 5 | HPMC | 6 | 121/15 |
| 14 | 2 | 20 | HPMC | 6 | 121/15 |
| 15 | 2 | 20 | HPMC | 10 | 121/15 |
| 16 | 2 | 5 | HPMC | 6 | 121/15 |
| 17 | 2 | 20 | HPMC | 3 | 121/15 |
| 18 | 2 | 5 | HPMC | 3 | 121/15 |
| 19 | 2 | 20 | HPMC | 3 | 121/15 |
| 20 | 2 | 10 | HPMC | 4.5 | 121/15 |
| 21 | 2 | 10 | HPMC | 4.5 | 121/15 |
| 22 | 2 | 10 | HEC | 3 | 121/15 |
| 23 | 2 | 10 | HEC | 3 | 121/15 |
| 24 | 2 | 30 | HEC | 1 | 121/15 |
| 25 | 2 | 10 | HA | 3.5 | 121/15* |
| 26 | 2 | 10 | HA | 2.5 | 121/15 |
| 27 | 2 | 30 | HEC | 1 | 121/15 |
| 28 | 2 | 30 | HA | 1 | 121/15* |
| 29 | 2 | 10 | HA | 2.5 | 121/15 |
| 30 | 2 | 10 | HA | 3.5 | 121/15 |
| 31 | 2 | 10 | HA | 4.5 | 121/15 |
| 32 | 2 | 30 | HA | 3.0 | 121/15 |
| 33 | 2 | 20 | HA | 1.5 | 121/15 |
| 34 | 2 | 20 | HA | 2.5 | 121/15 |
| 35 | 2 | 20 | HA | 3.5 | 121/15 |
| 36 | 2 | 10 | HA | 4 | 121/15, 121/30, and 123/15 |
| 37 | 2 | 10 | HA | 4 | 121/15, 121/30, and 123/15 |
| 38 | 2 | 10 | HA | 4 | 121/15, 121/30, and 123/15 |
| 39 | 2 | 35 | HA | 1 | 121/15* |
| 40 | 2 | 5 | HA | 3.5 | 121/15* |
| 41 | 2 | 10 | HA | 3.5 | 121/15* |
| 42 | 2 | 20 | HA | 2.0 | 121/15* |
| 43 | 2 | 20 | HA | 2.0 | 121/15* |
| 44 | 2 | 10 | HA | 3.5 | 121/15* |
| 45 | 2 | 10 | HA | 3.5 | 121/15* |
| 46 | 2 | 25 | N/A | 0 | 120/15 |
| 47 | 2 | 25 | N/A | 0 | 118/20 |
| 48 | 2 | 25 | N/A | 0 | 120/12 |
| HEC1 | 2 | 5 | HEC | 5 | 121/15 |
| HEC2 | 2 | 20 | HEC | 5 | 121/15 |
| HEC3 | 2 | 5 | HEC | 2 | 121/15 |
| HEC4 | 2 | 20 | HEC | 2 | 121/15 |
| HEC5 | 2 | 5 | HEC | 5 | 121/15 |
| HEC6 | 2 | 20 | HEC | 5 | 121/15 |
| HEC7 | 2 | 5 | HEC | 2 | 121/15 |
| HEC8 | 2 | 20 | HEC | 2 | 121/15 |
| HEC9 | 2 | 10 | HEC | 3 | 121/15 |
| PVP1 | 2 | 10 | PVP | 25 | 121/15 |
| PVP2 | 2 | 10 | PVP | 25 | 121/15 |

TABLE 3-continued

Autoclavable suspensions of cyclosporin A Form 2.

| Formulation | CsA (Crystal form) | CsA (%) | Gelling Agent (Type) | Gelling Agent (%) | Autoclave Conditions (Temp ° C./min) |
|---|---|---|---|---|---|
| PVP3 | 2 | 10 | PVP | 15 | 121/15 |
| PVP4 | 2 | 10 | PVP | 15 | 121/15 |
| PVP5 | 2 | 25 | PVP | 25 | 121/15 |
| PVP6 | 2 | 25 | PVP | 25 | 121/15 |
| PVP7 | 2 | 25 | PVP | 15 | 121/15 |
| PVP8 | 2 | 25 | PVP | 15 | 121/15 |
| PVP9 | 2 | 10 | PVP | 25 | 121/15 |
| PVP10 | 2 | 25 | PVP | 25 | 121/15 |

CsA = cyclosporin A.
CMC = carboxymethyl cellulose.
HPMC = hydroxypropyl methyl cellulose.
HEC = hydroxyethyl cellulose.
HA = hyaluronic acid.
PVP = polyvinylpyrrolidone.
*= slurry autoclaved prior to addition of gelling agent.

Methods of Preparation

Suspensions of the invention contain cyclosporin A Form 2 and a suspending agent. In another embodiment, the suspension also contains one or more of water, buffer, and salt, in sufficient quantities to provide a biocompatible formulation. By "biocompatible," the inventors mean that the suspension is appropriate for administration to the eye (for example, by parenteral administration).

The formulations of the invention may be manufactured by using either a heat-sterilized slurry of Form 2 cyclosporin mixed aseptically with a sterile parenterally-biocompatible suspending agent and other excipient; or by combining Form 2 cyclosporin with a parenterally-biocompatible suspending agent and other excipients and heat sterilizing the entire formulation.

These methods address various important problems with cyclosporin formulation: 1) solid cyclosporin cannot be pre-sterilized by irradiation without significant drug degradation and formation of degradation products; 2) sterile filtration is also not feasible because the formulation is a suspension; and 3) terminal sterilization by heat will decrease gel viscosity. Also, in one embodiment, the final viscosity of the drug formulation is sufficiently high to keep the cyclosporin suspended throughout the product's shelf-life. In another embodiment, the viscosity is sufficiently low to permit the final formulation to flow through a narrow gauge syringe, such as a 22, 23, 24, 25, or 26 gauge needle or narrower. In still another embodiment, the formulation is sufficiently high to keep the cyclosporin suspended throughout the product's shelf-life, and also sufficiently low to permit the final formulation to flow through a syringe with a 22, 23, 24, 25, or 26 gauge needle or narrower.

Methods 1 and 2, below, use hyaluronic acid as the suspending agent but, other suitable suspending agents may be substituted.

It should be noted that sterile hyaluronic acid is very expensive and that method 2 provides a unique method of sterilization, which allows the use of non-sterile hyaluronic acid by heat-reducing the polymer to the correct molecular weight range, so that it reaches the target viscosity range. Method 2, therefore, requires precision manufacturing, where each new lot of hyaluronic acid may shift to a different viscosity range, under identical manufacturing conditions. Consequently, in order to assure the correct viscosity range is reached in every commercial batch, the heat cycle will need to be adaptive—that is—adjusted according to a set of guidelines and experiments on the raw material lot prior to manufacture of the drug product.

Furthermore, it should be noted that Method 2 prepares all steps of the formulation in a single vessel. These two methods allow for the rapid production of the drug product and consequently, have substantial value in saving one day or more of valuable manufacturing time over Method 1.

These methods depend on the inventors' surprising discovery that cyclosporin A Form 2 may be autoclaved and still retain its potency and stability. Other forms of cyclosporin—amorphous, Form 1 and Form 3—cannot be autoclaved, without unacceptable loss of drug substance from the suspension.

Method 1—Aqueous Slurry Method

The appropriate amount of cyclosporin A Form 2 is suspended and mixed in phosphate buffered saline solution and the slurry is heat sterilized by autoclave. In an aseptic environment, the appropriate amount of pre-sterilized hyaluronic acid is added to the sterile cyclosporin slurry, is mixed, and then dissolved. The drug product is brought to volume with sterile water for injection. The final product has a viscosity in the correct range to create a long-term stable suspension, while allowing the final formulation to flow through a syringe fitted with a narrow-gauge needle, such as 25 gauge needle or narrower.

Method 2—Single Vessel Method

An excess of non-sterile hyaluronic acid is dissolved in phosphate buffered saline solution. Cyclosporin A Form 2 is suspended and mixed. The resulting suspension formulation is heat-sterilized by autoclave (using an "adaptive" heat cycle), at the appropriate temperature and for the appropriate amount of time, to both sterilize the formulation and bring the viscosity into the desired range.

For parenteral formulations, it may be desirable to achieve a viscosity that is sufficiently high to keep the cyclosporin suspended throughout the product's shelf-life, and also sufficiently low to permit the final formulation to flow through a syringe with a 22, 23, 24, 25, or 26 gauge needle or narrower. While hydrogel solutions are generally recognized as safe for topical use, very few have been used for parenteral administration, and none have been demonstrated to be safely injected through a 25 gauge needle (or narrower) into subconjunctival tissue at high hydrogel concentrations. A high concentration of suspending agent (up to 25%) is necessary in order to maintain the suspendability of the 5-40% cyclosporin parenteral formulations described herein. In one embodiment, parenteral formulations for use in subconjunctival tissue are (1) injectable through a narrow-gauge needle, such as 25 gauge or narrower, in order to minimize tissue damage by the needle, to allow for quick healing of the needle entry-point, and to limit the back-flow of the injected formulation; (2) sterile; (3) biocompatible; and (4) sufficiently viscous to maintain suspendability throughout the shelf-life of the formulation and to prevent tissue reflux out of the subconjunctival space. In such formulations viscosity is sufficiently high to retain long-term suspendability of the drug but sufficiently low to allow the entire formulation to readily pass through a narrow gauge needle.

In one embodiment of the invention, the formulations have a very high viscosity (e.g., ≥100,000 cps) yet may still able to be injected out of syringe through a narrow-gauge needle. The following table gives examples of such formulations.

|  | Formulation | | | | | |
| --- | --- | --- | --- | --- | --- | --- |
|  | 5% CsA, 3.5% HA (10203X) Viscosity: TBD | | 10% CsA, 3.5% HA (10204X) Viscosity: 1,300,000 cps | | 20% CsA, 2.0% HA (10205X) Viscosity: 700,000 cps | |
| Needle size and type | BD Precision Glide 27 G × 0.5" Needle | TSK Steriject 27 G × 0.5" UTW (Ultra Thin Wall) Needle | BD Precision Glide 27 G × 0.5" Needle | TSK Steriject 27 G × 0.5" UTW (Ultra Thin Wall) Needle | BD Precision-Glide 27 G × 0.5" Needle | TSK Steriject 27 G × 0.5" UTW (Ultra Thin Wall) Needle |
| Injectabiltiy | ✓ | ✓ | ✓ | ✓ | ✓ | ✓ |

Methods of Treatment

Compositions of the invention may be used to treat any condition of the eye which is known to be amenable to topical treatment with cyclosporin A (such as with Restasis®) at the concentrations stated here. For example, compositions of the invention may be used to treat patients suffering from dry eye, to treat blepharitis and meibomian gland disease, to restore corneal sensitivity that has been impaired due to refractive surgery on the eye, to treat allergic conjunctivitis and atopic and vernal keratoconjunctivitis, and to treat pterygium, conjunctival and corneal inflammation, keratoconjunctivitis, graft versus host disease, post-transplant glaucoma, corneal transplants, mycotic keratitis, Thygeson's superficial punctate keratitis, uveitis, and Theodore's superior limbic keratoconjunctivitis, among other conditions.

The International Dry Eye Workshop (DEWS) defines dry eye as "a multifactorial disease of the tears and ocular surface that results in symptoms of discomfort, visual disturbance, and tear film instability with potential damage to the ocular surface, accompanied by increased osmolarity of the tear film and inflammation of the ocular surface." It includes those conditions, such as keratoconjunctivitis sicca, that are caused by tear deficiency or excessive evaporation of tears.

Blepharitis is a chronic disorder producing inflammation of the anterior and posterior lid margin, with involvement of skin and its related structures (hairs and sebaceous glands), the mucocutaneous junction, and the meibomian glands. It can also affect the conjunctiva, tear film, and the corneal surface in advanced stages and may be associated with dry eye. Blepharitis is commonly classified into anterior or posterior blepharitis, with anterior affecting the lash bearing region of the lids, and posterior primarily affecting the meibomian gland orifices.

Meibomian gland disease most often occurs as one of three forms: primary meibomitis, secondary meibomitis, and meibomian seborrhea. Meibomian seborrhea is characterized by excessive meibomian secretion in the absence of inflammation (hypersecretory meibomian gland disease). Primary meibomitis, by contrast, is distinguished by stagnant and inspissated meibomian secretions (obstructive hypersecretory meibomian gland disease). Secondary meibomitis represents a localized inflammatory response in which the meibomian glands are secondarily inflamed in a spotty fashion from an anterior lid margin blepharitis.

Impaired corneal sensitivity often occurs after refractive surgery, such as photorefractive keratectomy, laser assisted sub-epithelium keratomileusis (LASEK), EPI-LASEK, customized transepithelial non-contact ablation, or other procedures in which the corneal nerves are severed. Impaired corneal sensitivity may also occur after viral infection, such as by HSV-1, HSV-2, and VZV viruses. Patients with impaired corneal sensitivity often complain that their eyes feel dry, even though tear production and evaporation may be normal, suggesting that "dryness" in such patients is actually a form of corneal neuropathy that results when corneal nerves are severed by surgery or inflamed after viral infection.

Allergic conjunctivitis is an inflammation of the conjunctiva resulting from hypersensitivity to one or more allergens. It may be acute, intermittent, or chronic. It occurs seasonally, that is, at only certain time of the year, or it occurs perennially, that is, chronically throughout the year. Symptoms of seasonal and perennial allergic conjunctivitis include, in addition to inflammation of the conjunctiva, lacrimation, tearing, conjunctival vascular dilation, itching, papillary hyperplasia, chemosis, eyelid edema, and discharge from the eye. The discharge may form a crust over the eyes after a night's sleep.

Atopic keratoconjunctivitis is a chronic, severe form of allergic conjunctivitis that often leads to visual impairment. Symptoms include itching, burning, pain, redness, foreign body sensation, light sensitivity and blurry vision. There is often a discharge, especially on awakening from a night's sleep; the discharge may be stringy, ropy, and mucoid. The lower conjunctiva is often more prominently affected than the upper conjunctiva. The conjunctiva may range from pale, edematous, and featureless to having the characteristics of advanced disease, including papillary hypertrophy, sub-epithelial fibrosis, formix fornix foreshortening, trichiasis, entropion, and madarosis. In some patients the disease progresses to punctate epithelial erosions, corneal neovascularization, and other features of keratopathy which may impair vision. There is typically goblet cell proliferation in the conjunctiva, epithelial pseudotubular formation, and an increased number of degranulating eosinophils and mast cells in the epithelium. CD25+T lymphocytes, macrophages, and dendritic cells (HLA-DR+, HLA-CD1+) are significantly elevated in the substantia propria.

Like atopic keratoconjunctivitis, vernal keratoconjunctivitis is a severe form of allergic conjunctivitis, but it tends to affect the upper conjunctiva more prominently than the lower. It occurs in two forms. In the palpebral form, square, hard, flattened, closely packed papillae are present; in the bulbar (limbal) form, the circumcorneal conjunctiva becomes hypertrophied and grayish. Both forms are often accompanied by a mucoid discharge. Corneal epithelium loss may occur, accompanied by pain and photophobia, as may central corneal plaques and Trantas' dots.

EXAMPLES

The invention is further illustrated by the following examples.

When the inventors autoclaved aqueous suspensions of cyclosporin A, the drug particles aggregated, making the product unacceptable. Additionally, the inventors found that hyaluronic acid also degrades upon autoclaving, causing a marked drop in viscosity. Lower viscosity, in turn, reduces the suspendability of the drug particles and causes them to settle. Formulations having drug particles in suspension that too rapidly settle, or irreversibly settle, may be useful for laboratory tests, but are not commercially viable.

The inventors explored formulations of four cyclosporin A polymorphic forms, the amorphous form, the tetragonal crystalline form (form 1), the orthorhombic form (form 3), and cyclosporin A Form 2.

Figure 3:
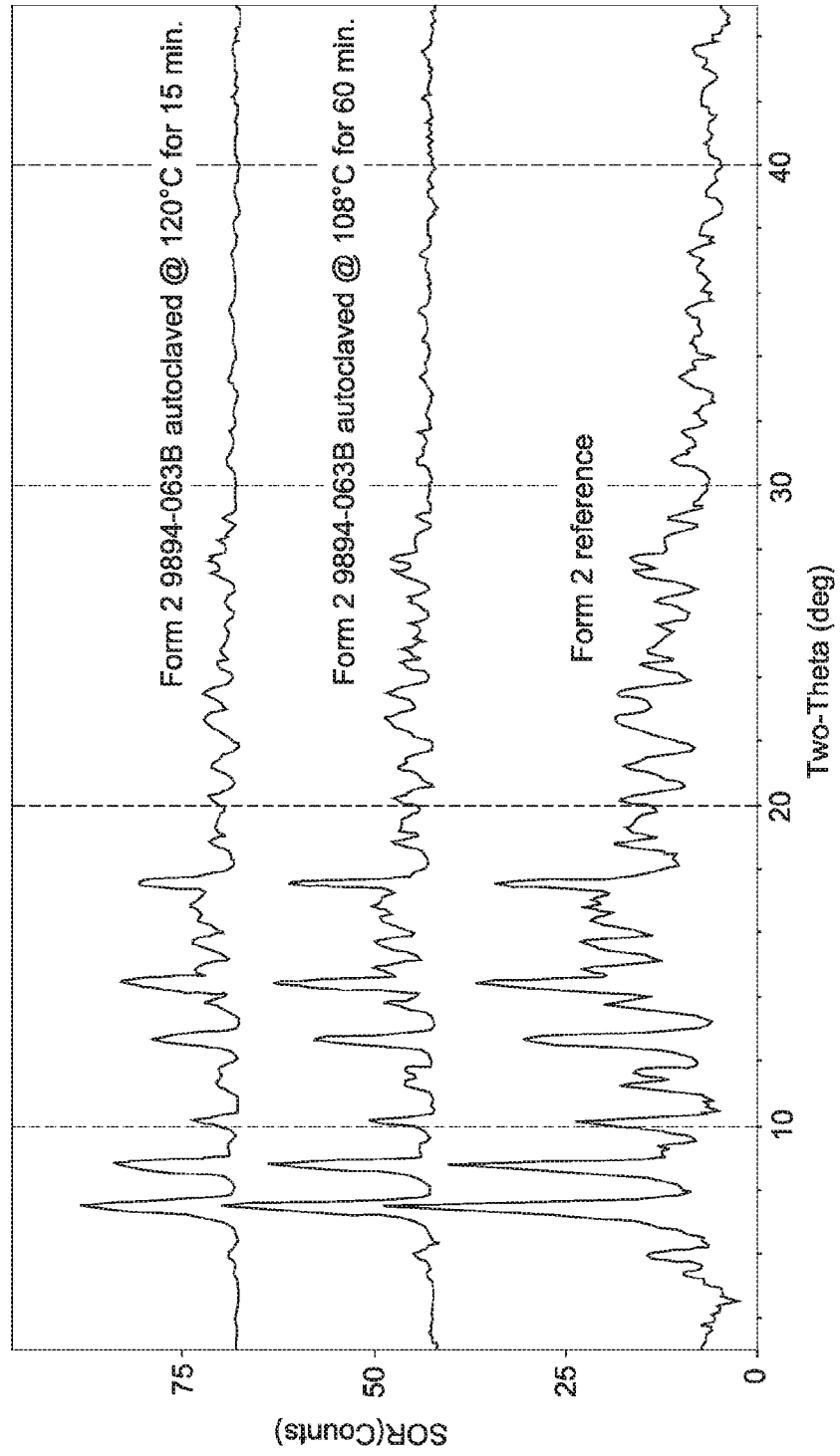
FIG. 3 shows x-ray powder diffraction pattern data of cyclosporin A Form 2 after autoclaving.

A suspension of form 1 converts to the amorphous form and aggregates upon autoclaving; clumping of the cyclosporin is also observed. Consequently, neither form 1 nor the amorphous form is suitable for autoclave stabilization. Furthermore, an autoclaved suspension of F3 in water lost 11-28% of its potency during autoclaving (Table 4); this, too, is unacceptable. In contrast, a suspension of Form 2 in water was quite stable to autoclaving, resisting degradation when compared to a pre-sterilization control. X-ray analysis of filtered solid from the Form 2 formulation also confirms that Form 2 is polymorphically stable to autoclaving (FIG. 3). These latter two findings are extremely surprising, considering the lack of either chemical or polymorphic stability of the other three forms.

The inventors explored the autoclavability of a series of concentrated solutions of various polymers (no drug) which, when loaded in a syringe, will flow through a narrow-gauge needle (25 gauge or narrower). The polymers evaluated were as follows: crosslinked hyaluronic acid (Juvederm®), carbomer, carboxymethylcellulose-medium molecular weight, carboxymethylcellulose-high molecular weight, hydroxyethylcellulose, hydroxypropylcellulose, Pluronic F127 and polyvinylpyrrolidone K90. All of these are readily available from commercial suppliers.

Figure 4:
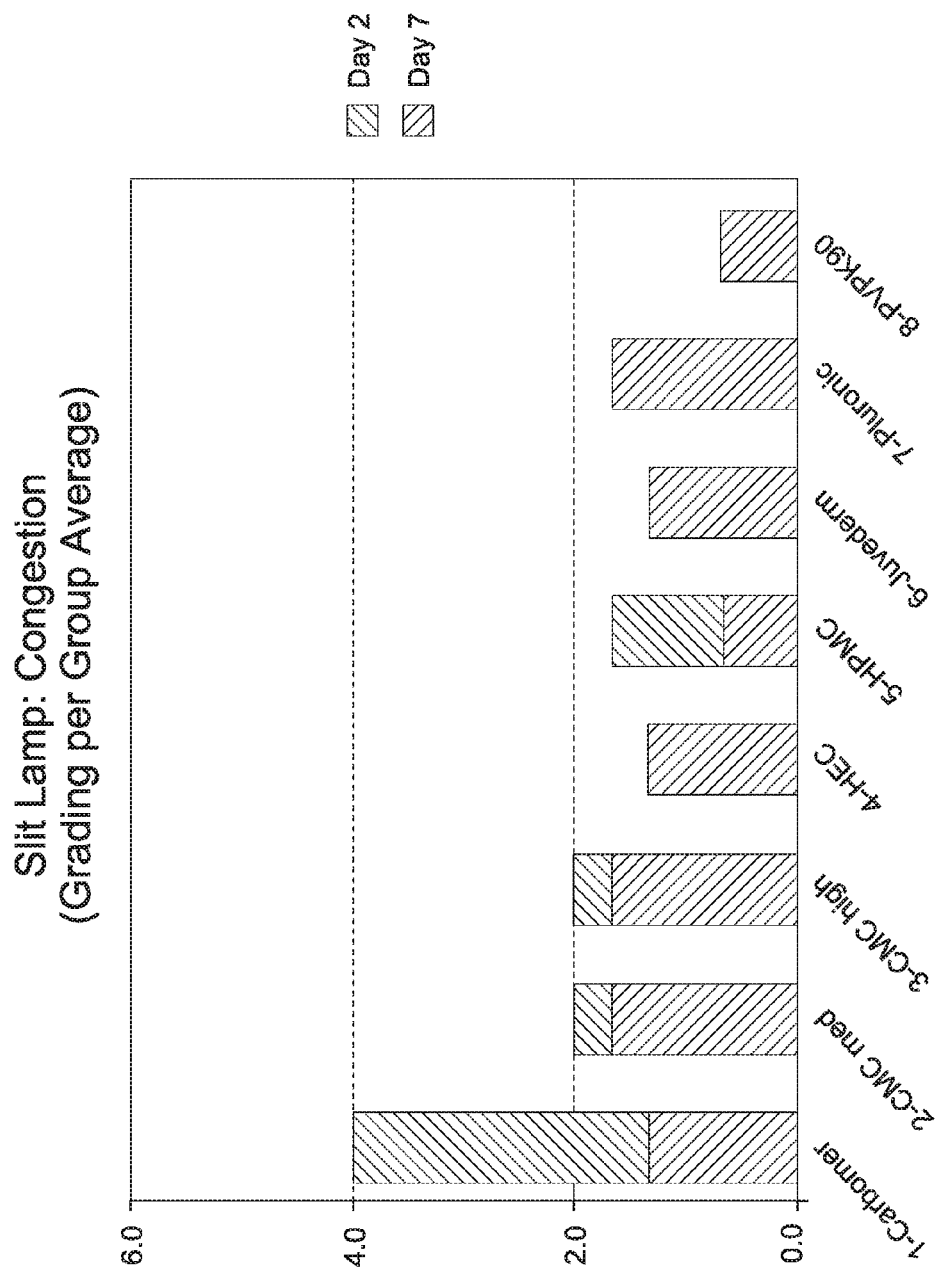
FIG. 4 shows congestion seen on slit lamp examination with eight different formulations.
Figure 5:
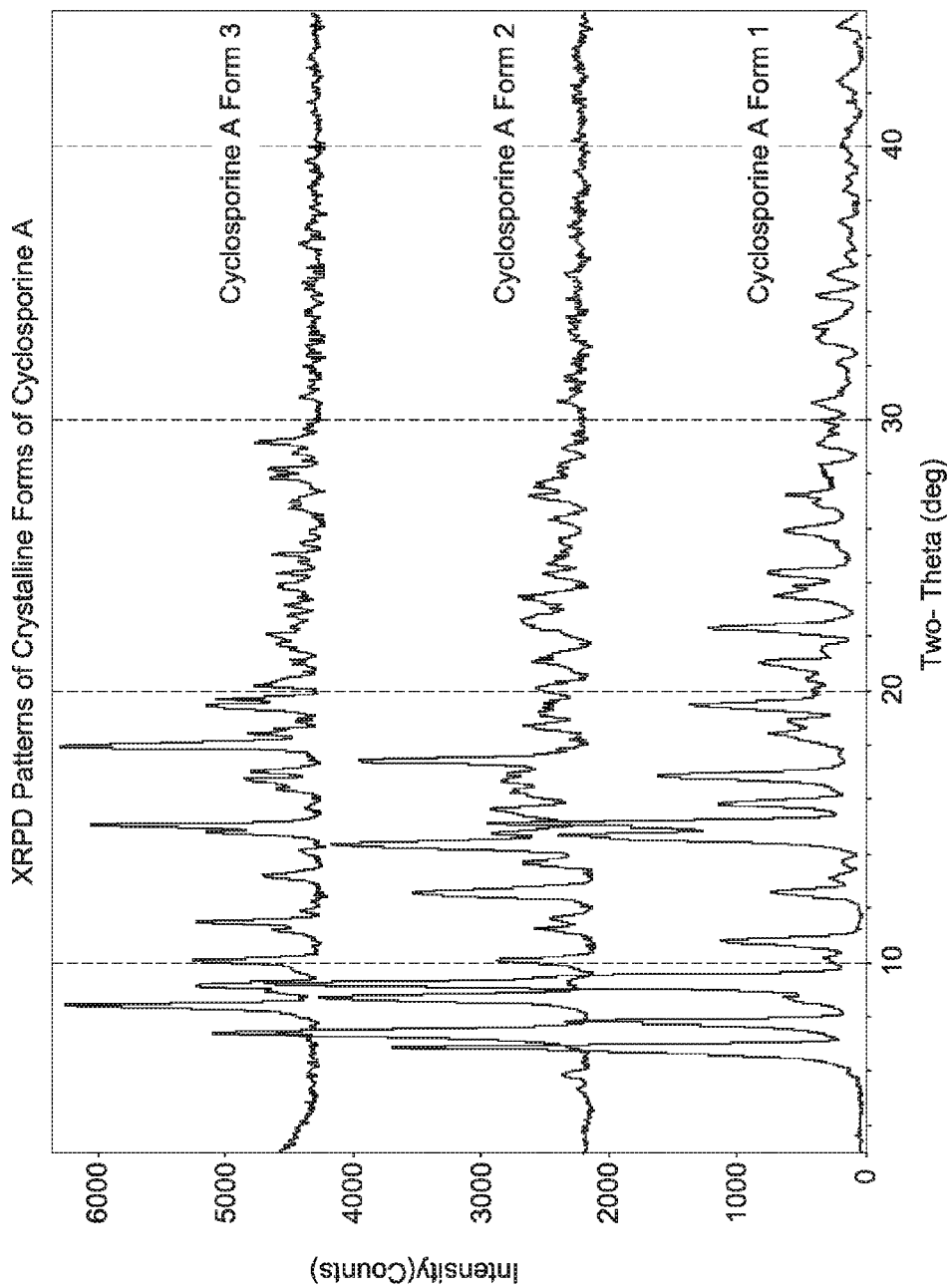
FIG. 5 depicts characteristic X-ray powder diffraction (XRPD) patterns of CsA in a new crystalline form (desig nated as Form 2 herein), tetragonal form (designated as Form 1 herein), and orthorhombic form (designated as Form 3 herein).
Figure 6:
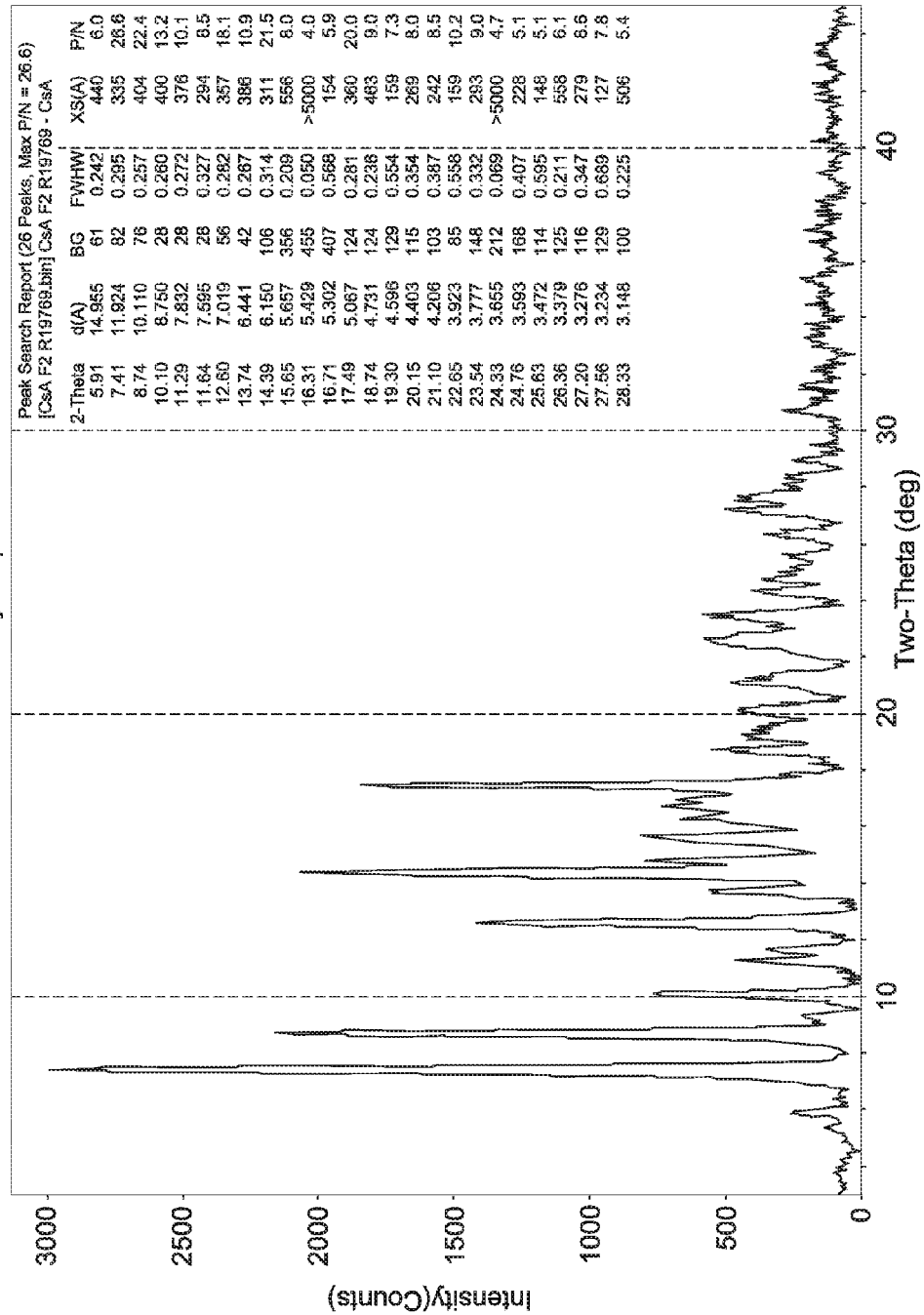
FIG. 6 depicts the XRPD diffractogram of CsA crystalline Form 2.

One hundred microliters of each of the autoclaved solutions was injected into rabbit conjunctiva, in order to evaluate the propensity for causing inflammation. Those polymers producing an inflammatory reaction were eliminated from consideration (FIG. 4, carbomer, both CMC's, and HPMC were eliminated). Additionally, Juvederm® was eliminated because it formed a long-lasting bleb which, in humans, might cause irritation as the eyelid moves over the site of injection. Both HPMC and Pluronic separated from the solution during/after autoclaving and consequently were also eliminated. Of the commercially viable hydrogels, only HEC and PVP demonstrated that they produced no inflammation in rabbit conjunctiva after autoclaving. These two hydrogels were used to formulate cyclosporin A suspensions for further evaluation. The results of the studies are shown in Table 5.

Initially, the inventors explored the possibility of heat-sterilizing a slurry of cyclosporin A of Form 1 (which converts to the amorphous form). This approach resulted in agglomeration of the drug and consequently, the formulation was not viable. Further studies, adding PVP to suppress the agglomeration of Form 1/amorphous form, also failed.

Figure 2:
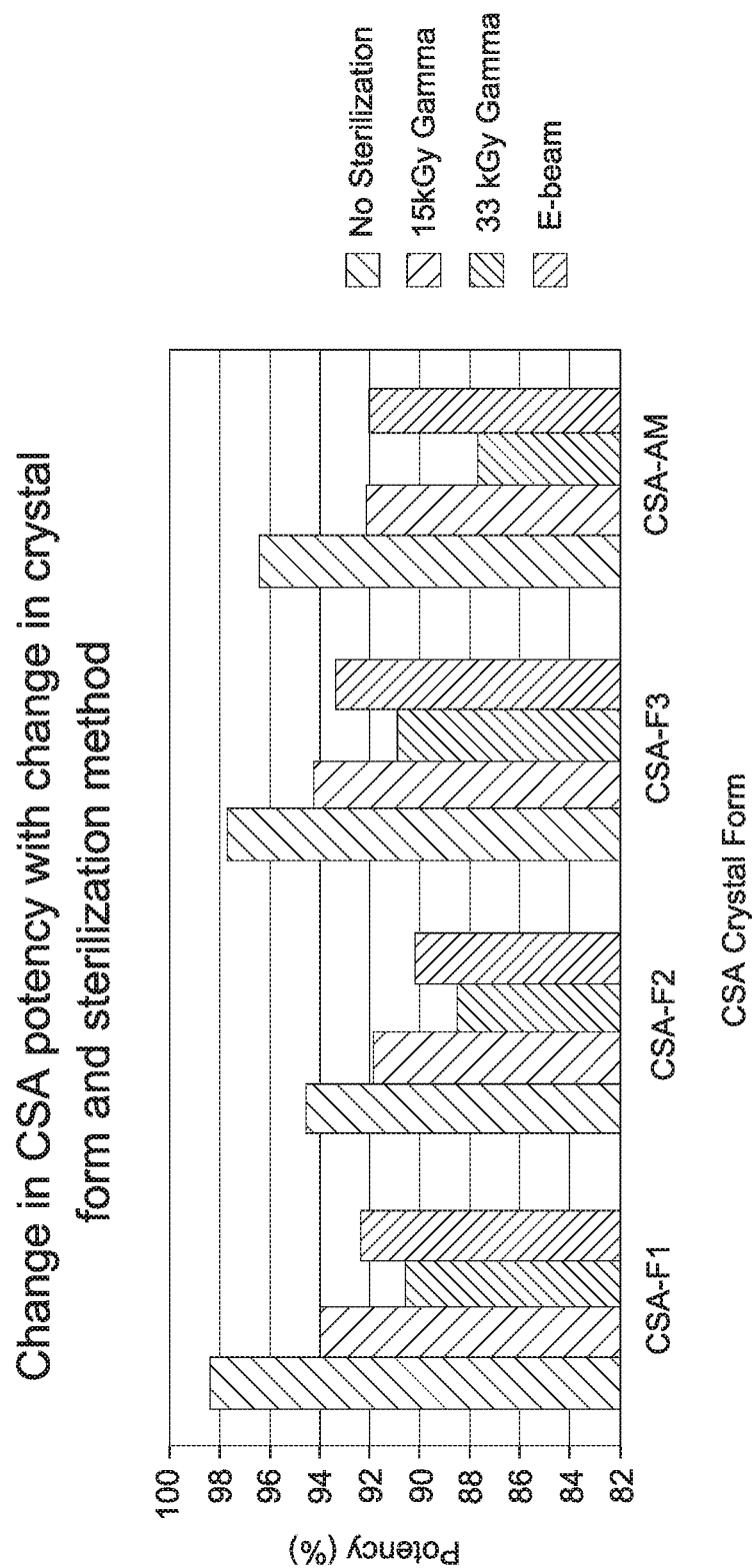

Since heat-sterilization of an aqueous suspension of cyclosporin did not appear to be viable, the inventors planned to prepare suspensions by aseptic technique, using pre-sterilize solid cyclosporin. Various solid cyclosporins (Forms 1, 2, and 3 and amorphous) were treated with gamma or e-beam irradiation. In all cases, significant loss of drug (3-9%) occurred (FIG. 2 and Table 1). Furthermore, the substantial loss of drug indicates that high levels of degradation products (around 3-9%) are generated in the irradiation-sterilized material. These impurities may have negative toxicological and/or regulatory implications; consequently, this approach to sterilization appears to be undesirable.

TABLE 1

Effect of Irradiation Sterilization on Cyclosporin (CsA) Drug Substance (solid)

| Sterilization Mode | Form 1 CsA (Potency and Imp.) | Form 2 CsA (Potency and Imp.) | Form 3 CsA (Potency and Imp.) | Amorph. CsA (Potency and Imp.) |
|---|---|---|---|---|
| None | 98.4% w/w Total Imp: 0.6% | 94.6% w/w Total Imp: 0.6% | 97.7% w/w Total Imp: 0.8% | 96.5% w/w Total Imp: 0.7% |
| 15 kGy Gamma | 93.9% w/w % Rel. Change: 4.5% Total Imp: 1.7% | 91.8% w/w % Rel. Change: 2.9% Total Imp: 1.8% | 94.3% w/w % Rel. Change: 3.6% Total Imp: 1.3% | 92.1% w/w % Rel. Change: 4.6% Total Imp: 1.4% |
| 33 kGy Gamma | 90.7% w/w % Rel. Change: 7.8% Total Imp: 2.8% | 88.5% w/w % Rel. Change: 6.4% Total Imp: 2.4% | 91.0% w/w % Rel. Change: 6.9% Total Imp: 2.3% | 87.7% w/w % Rel. Change: 9.2% Total Imp: 2.3% |
| E-Beam | 92.6% w/w % Rel. Change: 5.9% Total Imp: 1.5% | 90.3% w/w % Rel. Change: 4.6% Total Imp: 1.7% | 93.4% w/w % Rel. Change: 4.5% Total Imp: 1.6% | 92.0% w/w % Rel. Change: 4.7% Total Imp: 1.3% |

Subsequently, the inventors attempted to irradiate solid cyclosporin (Forms 1, 2, and 3 and amorphous), under the best conditions above, at cold temperatures. No significant improvement was noted with any of the Forms of cyclosporin (Table 2).

TABLE 2

Effect of E-Beam Sterilization of Cyclosporins under Cold Conditions

| CsA Drug Substance Sample Treatment | CsA Potency for Control Sample | CsA Potency 15 kGy Gamma Treatment | CsA Potency 30 kGy Gamma Treatment | CsA Potency E-Beam 15 kGy Treatment |
|---|---|---|---|---|
| Dry Ice | 99.2% w/w | 96.7% w/w (% Rel. Change: 2.5%) | 93.8% w/w (% Rel. Change: 5.4%) | 93.8% w/w (% Rel. Change: 5.4%) |
| Cold Pack | 96.5% w/w | 93.0% w/w (% Rel. Change: 3.6%) | 92.1% w/w (% Rel. Change: 4.6%) | 93.2% w/w (% Rel. Change: 3.4%) |

After it became apparent that irradiation of solid cyclosporins produced too much degradation, the inventors attempted to irradiate an aqueous suspension of cyclosporin, using hyaluronic acid as a suspending agent. This approach resulted in 4-10% degradation of the drug within the formulation.

TABLE 3

Effect of Sterilization by Irradiation on Aqueous Suspensions of Cyclosporin [CsA] using Hyaluronic Acid [HA] as a Suspending Agent, at Various Temperatures

| Sterilization Treatment | CsA Potency for Control Sample | CsA Potency Post-Sterilization | % Relative Change in Potency |
|---|---|---|---|
| Cold Pack Control CsA Hydrogel Sample | 103.2% w/w | Not Applicable | Not Applicable |
| CsA-HA Sample (Cold Pack) Treated with 15 kGy Gamma | 103.2% w/w | 98.9% w/w | 4.2% |
| CsA-HA Sample (Cold Pack) Treated with 30 kGy Gamma | 103.2% w/w | 92.3% w/w | 10.6% |
| CsA-HA Sample (Cold Pack) Treated with E-Beam (15 kGy) | 103.2% w/w | 92.8% w/w | 10.1% |

Finally, the inventor turned their focus on steam sterilization of slurries and full formulations of cyclosporins. Slurries of Form 1 (which converts to amorphous) agglomerate during heat-sterilization. Slurries of Form 3, while physically stable and more chemically stable than Form 1, degraded significantly during heat sterilization. But, to the inventors' surprise, slurries of Form 2 were both physically and chemically stable (Tables 4 and 5).

TABLE 4

Heat-Sterilization of Slurries of Cyclosporin (ScA) Form 2 (F-2) in Water

|  | CsA-F2 Slurry % | CsA-F3 Slurry % |
|---|---|---|
| Initial | 96.86 | 101.41 |
| 120 C. 15 min | 96.88 | 88.61 |
| 108 C. 60 min | 106.69 | 71.72 |

TABLE 5

Physical Stabiltiy of Forms 2 and 3 Before and After Heat Sterilization

| Formulation | Material | Spec. | D90 | D50 | D10 | Conditions |
|---|---|---|---|---|---|---|
| A | CsA-F2 | Slurry control | 198.6313 | 116.8544 | 8.2711 | Slurry control for steam sterilization study |
| A, autoclaved | CsA-F2 | Autoclaved slurry | 186.4431 | 99.902 | 7.0518 | Autoclaved at 120 C. for 15 minutes |
| A, autoclaved | CsA-F2 | Autoclaved slurry | 195.603 | 112.532 | 9.209 | Autoclaved at 108 C. for 60 minutes |
| B | CsA-F3 | Slurry control | 110.8281 | 63.3348 | 7.1711 | Slurry control for steam sterilization study |
| B, autoclaved | CsA-F3 | Autoclaved slurry | 116.8761 | 67.523 | 12.1564 | Autoclaved at 120 C. for 15 minutes |
| B, autoclaved | CsA-F3 | Autoclaved slurry | 115.556 | 65.3309 | 10.5518 | Autoclaved at 108 C. for 60 minutes |

| Formulation | Material | Conditions | % potency compared to CsA Form 2 standard |
|---|---|---|---|
| A | CsA-F2 | Control | 96.9 |
| A | CsA-F2 | 120° C., 15 min | 96.9 |
| A | CsA-F2 | 108° C., 60 min | 106.7 |
| B | CsA-F3 | Control | 101.4 |
| B | CsA-F3 | 120° C., 15 min | 88.6 |
| B | CsA-F3 | 108° C., 60 min | 71.7 |

Ocular Congestion

Parenterally-biocompatible suspending agents were identified by injecting sterile concentrated solutions into the subconjunctival space and evaluating the toxicological response. An injection of 100 ul of the following polymers in phosphate buffered saline was administered subconjunctivally to New Zealand white rabbits and observed for a period of seven days.

| | type | name | source | Lot# | tech info | vendor | CoA | Grade | Alternative vendor | Grade |
|---|---|---|---|---|---|---|---|---|---|---|
| 1 | PVP | PVP K30 | Sigma_Aldrich 81420-500G (or PSO R14247) | BCBB7859 | Mw 40K (PSO: 5% in water, pH 3.6) | Sigma_Aldrich | yes | | BASF | PHEUR/USP/NF/JP |
| 2 | PVP | PVP K90 | Sigma_Aldrich 81440-250G | BCBB3954 | Mw 360K | Sigma_Aldrich | yes | | BASF | PHEUR/USP/NF/JP |
| 3 | PVP | PVP 10 | Sigma-Aldrich PVP10-500G | 050M0039 | Mw 10K | Sigma_Aldrich | yes | | BASF | PHEUR/USP/NF |
| 4 | HPMC | Hypromellose (tested to JP) | PSO PM# 1018 (R19424) | XB14012N11 | Sigma H3785: 4000 cP, 2% in water | Dow Chemical | yes | USP/PHEUR | | |
| 5 | CMC | Carboxymethyl cellulose sodium | PSO R19716Q pending | 96413 | | | | | CMC from Ashland/Aqualon is NF/USP, | |
| 6 | CMC | Carboxymethyl cellulose sodium | PSO R19717 | 96077 | | | | | | |
| 7 | Hydroxyethyl cellulose (HEC) | Natrosol (Type 250-HHX pharm) | Kevin Warner | F0854 | Type 250-HHX pharm | Ashland | | | HEC from Ashland./Aqualon is USP/EP, | |
| 8 | Acrylate/C10-30 Alkyl acrylate | Carbopol ETD 2020NF | Kevin Warner | EC742EK343 | acrylate crosspolymer (Viscosity, 47-77K cP 0.5% wt at pH 7.5) | Lubrizol | | USP/NF | | |
| 9 | Carbomer Interpolymer | Carbopol Ultrez 10 NF polymer | Kevin Warner | CC83RZG726 | type A (Viscosity, 45-65K cP 0.5% wt at pH 7.5) | Lubrizol | | USP/NF | | |
| 10 | Carbomer-Homopolymer | Carbopol 980 NF polymer | Kevin Warner | EC863CC625 | type C (Viscosity, 40-60K cP 0.5% wt at pH 7.5) | Lubrizol | | USP/PHEUR/JPE | | |
| 1 | PVP | PVP K30 | Sigma_Aldrich 81420-500G (or PSO R14247) | BCBB7859 | Mw 40K (PSO: 5% in water, pH 3.6) | Sigma_Aldrich | yes | | BASF | PHEUR/USP/NF/JP |
| 2 | PVP | PVP K90 | Sigma_Aldrich 81440-250G | BCBB3954 | Mw 360K | Sigma_Aldrich | yes | | BASF | PHEUR/USP/NF/JP |
| 3 | PVP | PVP 10 | Sigma-Aldrich PVP10-500G | 050M0039 | Mw 10K | Sigma_Aldrich | yes | | BASF | PHEUR/USP/NF |
| 4 | HPMC | Hypromellose (tested to JP) | PSO PM# 1018 (R19424) | XB14012N11 | Sigma H3785: 4000 cP, 2% in water | Dow Chemical | yes | USP/PHEUR | | |
| 5 | CMC | Carboxymethyl cellulose sodium | PSO R19716Q pending | 96413 | | | | | CMC from Ashland/Aqualon is NF/USP, | |
| 6 | CMC | Carboxymethyl cellulose sodium | PSO R19717 | 96077 | | | | | | |
| 7 | Hydroxyethyl cellulose (HEC) | Natrosol (Type 250-HHX pharm) | Kevin Warner | F0854 | Type 250-HHX pharm | Ashland | | | HEC from Ashland./Aqualon is USP/EP, | |
| 8 | Acrylate/C10-30 Alkyl acrylate | Carbopol ETD 2020NF | Kevin Warner | EC742EK343 | acrylate crosspolymer (Viscosity, 47-77K | Lubrizol | | USP/NF | | |

-continued

| | type | name | source | Lot# | tech info | vendor | CoA | Grade | Alternative vendor | Grade |
|---|---|---|---|---|---|---|---|---|---|---|
| 9 | Carbomer Interpolymer | Carbopol Ultrez 10 NF polymer | Kevin Warner | CC83RZG726 | cP 0.5% wt at pH 7.5) type A (Viscosity, 45-65K cP 0.5% wt at pH 7.5) | Lubrizol | | USP/ NF | | |
| 10 | Carbomer-Homopolymer | Carbopol 980 NF polymer | Kevin Warner | EC863CC625 | type C (Viscosity, 40-60K cP 0.5% wt at pH 7.5) | Lubrizol | | USP/ PHEUR/ JPE | | |

2% Carbomer (Carbopol Ultrez 10NF, Lubrizol)
8% Carboxymethyl Cellulose (low viscosity CMC, Lubrizol)
6% Carboxymethyl Cellulose (high viscosity CMC, Lubrizol)
6% HEC (Ashland)
6% HPMC (Dow Chemical)
Juvederm Ultra (Allergan, Inc)
Pluronic F127 (BASF)
Polyvinyl pyrrolidone (PVP K90, BASF)

Figure 9:
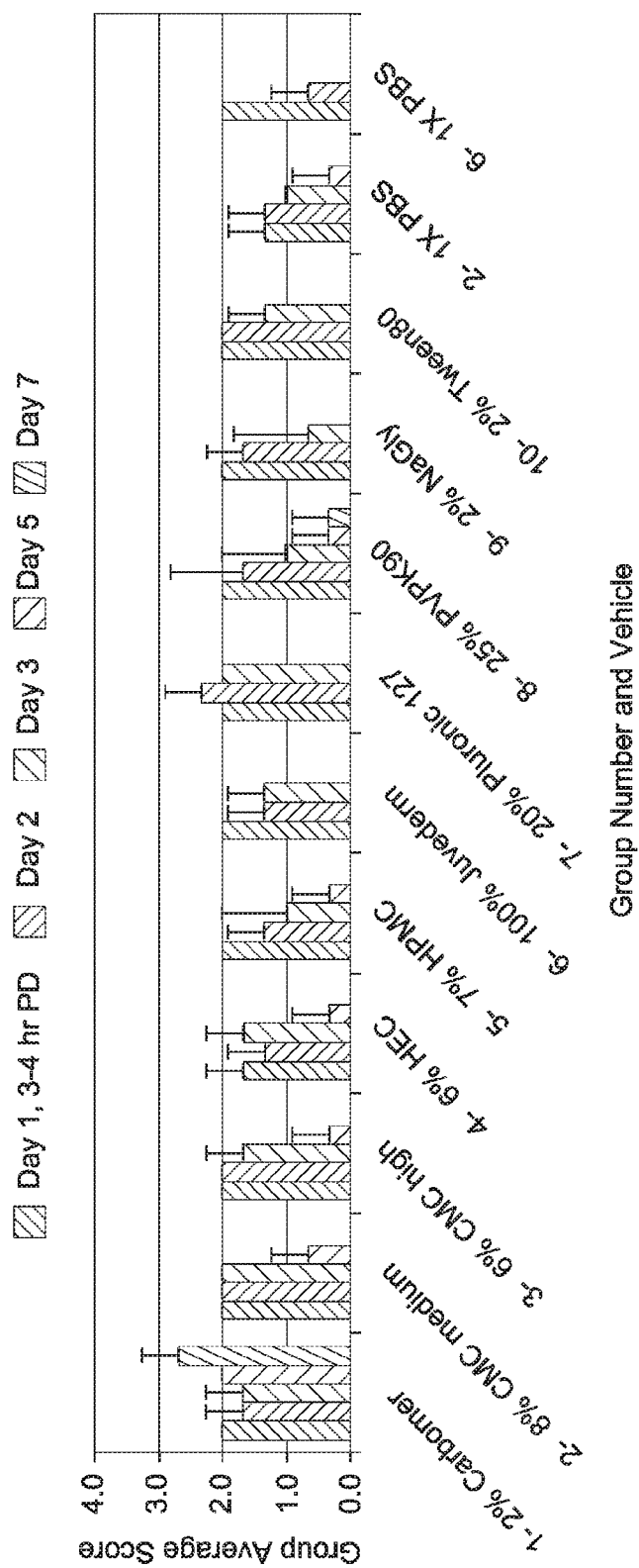
FIG. 9 shows gross ocular congestion after an injection of 100 ul of CMC, HEC, HPMC, Pluronic and PVP in phosphate buffered saline was administered subconjunctivally to New Zealand white rabbits. The rabbits were observed for seven days.
Figure 10:
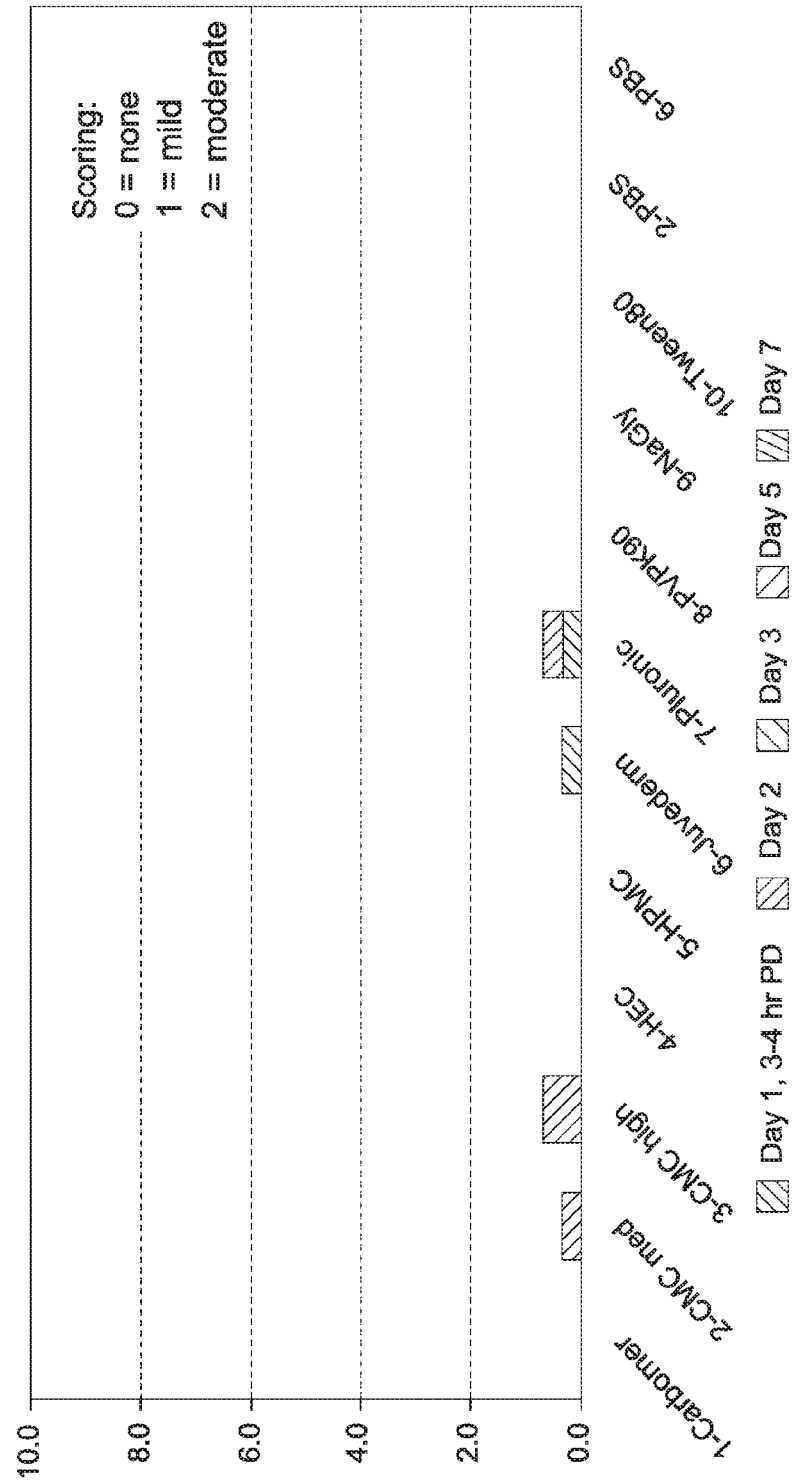
FIG. 10 shows gross ocular discharge in the experiment described in FIG. 9.
Figure 11:
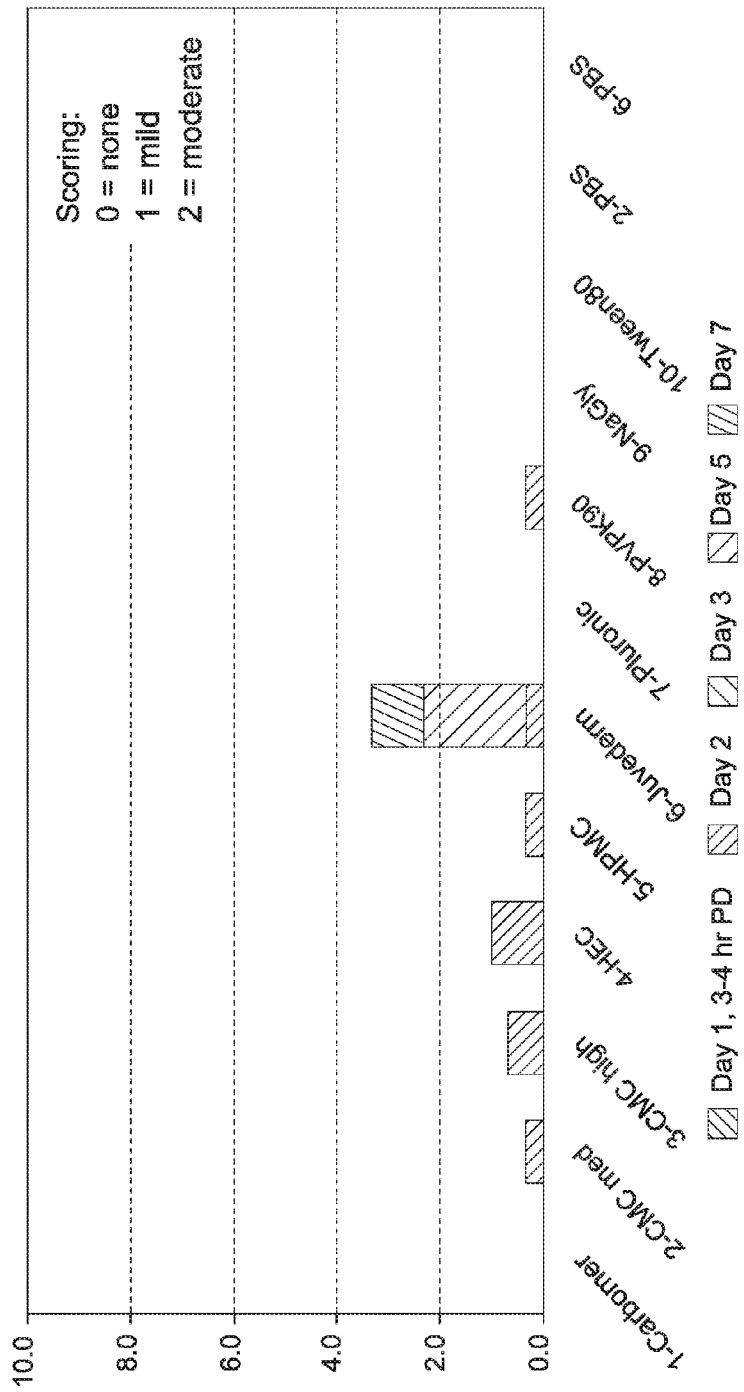
FIG. 11 shows gross ocular swelling in the experiment described in FIG. 9.

Gross ocular congestion was shown to resolve within 7 days for CMC, HEC, HPMC, Pluronic and PVP. Ocular discharge was shown to resolve within three days. Ocular discharge resolved within 3 days for all groups except one. Results of the experiment are provided in FIGS. 9-11.

Impurity and Potency Analysis

The inventors prepared various formulations and evaluated their potency and purity, as well particle size distribution.

| CsA Crystal | | | Autoclave Conditions Temp (° C.)/Time | Particle size distribution | | |
|---|---|---|---|---|---|---|
| Lot # | Form | Excipient | (min.) | D90 | D50 | D10 |
| 1 | 2 | 5% CMC | None | 52.38 | 10.80 | 5.31 |
| 2 | 2 | 5% CMC | 121/10 | 18.02 | 11.55 | 5.74 |

| | Composition | | | | | Impurities Analysis | | |
|---|---|---|---|---|---|---|---|---|
| | CsA Particle Size (µm) | CsA (%) | HEC (%) | Potency (%) | | Pre-Autoclave CsA Total Impurities (% a/a) | Post-Autoclave CsA Total Impurities (% a/a) | Absolute Change (% a/a) |
| Formulation | | | | No autoclave | Autoclave | | | |
| HEC-1 | 10 | 5 | 5 | 117.20% | 115.70% | 0.71% | 0.69% | −0.02% |
| HEC-2 | 10 | 20 | 5 | 103.60% | 116.60% | 0.61% | 0.61% | 0.00% |
| HEC-3 | 10 | 5 | 2 | 116.40% | 118.80% | 0.78% | 0.70% | −0.08% |
| HEC-4 | 10 | 20 | 1 | 124.50% | 124.70% | 0.73% | 0.69% | −0.04% |
| HEC-5 | 25 | 5 | 5 | 126.70% | 116.60% | 0.58% | 0.58% | 0.00% |
| HEC-6 | 25 | 20 | 5 | 140.00% | 147.40% | 0.56% | 0.56% | 0.00% |
| HEC-7 | 25 | 5 | 2 | 137.50% | 142.50% | 0.63% | 0.59% | −0.04% |
| HEC-8 | 25 | 20 | 2 | 129.50% | 119.70% | 0.56% | 0.57% | 0.01% |
| HEC-9 | 10 | 10 | 3 | 118.60% | 111.70% | 0.61% | 0.62% | 0.01% |

| | Composition | | | | |
|---|---|---|---|---|---|
| | CsA Particle Size (µm) | CsA (%) | PVP90 (%) | Potency (%) | |
| Formulation | | | | No autoclave | Autoclave |
| PVP-1 | 10 | 5 | 25 | 102.51 | 101.01 |
| PVP-2 | 10 | 20 | 25 | 113.81 | 111.82 |
| PVP-3 | 10 | 5 | 15 | 122.42 | 114.04 |
| PVP-4 | 10 | 20 | 15 | 120.28 | 123.3 |
| PVP-5 | 25 | 5 | 25 | 118.56 | 118.46 |
| PVP-6 | 25 | 20 | 25 | 114.55 | 115.28 |
| PVP-7 | 25 | 5 | 15 | 116.37 | 115.66 |
| PVP-8 | 25 | 20 | 15 | 120.9 | 124.05 |
| PVP-9 | 10 | 10 | 25 | 132.51 | 136.36 |
| PVP-10 | 25 | 10 | 25 | 118.03 | 126.6 |

| CsA Crystal | | | Autoclave Conditions Temp (° C.)/Time | Particle size distribution | | |
|---|---|---|---|---|---|---|
| Lot # | Form | Excipient | (min.) | D90 | D50 | D10 |
| 3 | 3 | 3% CMC | None | 28.01 | 12.09 | 6.84 |
| 4 | 3 | 3% CMC | 121/10 | 20.31 | 11.27 | 6.56 |
| 5 | 2 | None | None | 198.63 | 116.85 | 8.27 |
| 6 | 2 | None | 120/15 | 186.44 | 99.90 | 7.05 |
| 7 | 2 | None | 108/60 | 195.60 | 112.53 | 9.21 |
| 8 | 3 | None | None | 110.83 | 63.33 | 7.17 |
| 9 | 3 | None | 121/15 | 116.88 | 67.52 | 12.16 |
| 10 | 3 | None | 108/60 | 115.56 | 65.33 | 10.55 |
| 11 | 2 | None | None | 13.15 | 9.12 | 6.17 |
| 12 | 2 | None | 121/15 | 14.15 | 9.12 | 6.42 |

-continued

| Lot # | CsA Crystal Form | Excipient | Autoclave Conditions Temp (° C.)/Time (min.) | Particle size distribution D90 | D50 | D10 |
|---|---|---|---|---|---|---|
| 13 | 2 | None | None | 14.14 | 9.66 | 6.44 |
| 14 | 2 | None | 121/15 | 14.30 | 9.37 | 5.95 |

TABLE 5

Key F2 Formulation Properties of Evaluated Polymers

| | Syringeability | Autoclavability (121 C., 15 min.) | In-vivo tolerability (1 wk sub-conj.) | Settling | CSA-F2 Potency |
|---|---|---|---|---|---|
| Carbopol | Max. conc. 4% w/22 G | No visible change | Poorly tolerated (congestion) | na | na |
| Carboxymethyl Cellulose (CMC) medium viscosity | Max. conc. 9% w/22 G | No visible change | Poorly tolerated (congestion) | na | na |
| Carboxymethyl Cellulose (CMC) high viscosity | Max. conc. 6% w/22 G | No visible change | Poorly tolerated (congestion) | na | na |
| Hydroxyethyl Cellulose (HEC) | Max. conc. 6% w/22 G | No visible change | Well tolerated. Slight congestion compared to saline. | No settling in comparison with BDP gel under same conditions | No loss in potency post-autoclave |
| Hydroxypropyl Methyl Cellulose (HPMC) | Max. conc. 7% w/22 G | Full formation visibly separates with moist heat sterilization | Well tolerated. Comparable to saline. | na | na |
| Juvederm Ultra | 30 g, as formulated by manufacturer | Pre-sterilized by manufacturer | poorly tolerated (swelling at 1 week) | na | na |
| Pluronic F127 | Max. cone. 40% w/22 G | Placebo visibly separates with moist heat sterilization | Tolerated. Slight congestion and discharge compared to saline. | na | na |
| Polyvinylpyrrolidone K90 (PVPK90) | Max. conc. 27% w/22 G | No visible change | Ok | Some settling with syringeable concentrations (but acceptable) | No loss in potency post-autoclave |

What is claimed is:

1. A method of making a formulation of cyclosporin A, the method comprising the steps of a) dissolving cyclosporin A form 2 in solution;

b) autoclaving the solution; and c) adding a vehicle selected from the group consisting of carboxymethyl cellulose, hydroxypropyl methyl cellulose, hydroxyethyl cellulose, hyaluronic acid, polyvinylpyrrolidone, crosslinked polyacrylic acid polymers, and copolymers based on ethylene oxide and propylene oxide.

2. A method of making a formulation of cyclosporin A, the method comprising the steps of a) dissolving in solution a vehicle selected from the group consisting of carboxymethyl cellulose, hydroxypropyl methyl cellulose, hydroxyethyl cellulose, hyaluronic acid, polyvinylpyrrolidone, crosslinked polyacrylic acid polymers, and copolymers based on ethylene oxide and propylene oxide;

b) adding to the solution cyclosporin A Form 2; and c) autoclaving the resulting mixture.

* * * * *